US008927600B2

(12) United States Patent
Le Guern et al.

(10) Patent No.: US 8,927,600 B2
(45) Date of Patent: Jan. 6, 2015

(54) COMPOUND FOR USE IN THE TREATMENT OF PERIPHERAL NEUROPATHIES

(75) Inventors: Marie-Emmanuelle Le Guern, Compiegne (FR); Marc Verleye, Remy (FR); Jean-Marie Gillardin, Jonquieres (FR); Bernard Hublot, Compiegne (FR)

(73) Assignee: Biocodex, Gentilly (FR)

( * ) Notice: Subject to any disclaimer, the term of this patent is extended or adjusted under 35 U.S.C. 154(b) by 835 days.

(21) Appl. No.: 12/726,946

(22) Filed: Mar. 18, 2010

(65) Prior Publication Data

US 2010/0240588 A1    Sep. 23, 2010

(30) Foreign Application Priority Data

Mar. 19, 2009  (FR) ..................................... 09 51766

(51) Int. Cl.
| | | |
|---|---|---|
| *A61K 31/357* | (2006.01) | |
| *A61K 31/343* | (2006.01) | |
| *A61P 25/02* | (2006.01) | |
| *A61K 31/36* | (2006.01) | |
| *A61K 45/06* | (2006.01) | |

(52) U.S. Cl.
CPC ............... *A61K 31/357* (2013.01); *A61K 31/36* (2013.01); *A61K 45/06* (2013.01)
USPC ............................ 514/464; 568/579; 568/608

(58) Field of Classification Search
CPC ........................... A61K 31/357; A61K 31/343
USPC ............... 514/12, 34, 283, 464; 568/579, 608
See application file for complete search history.

(56) References Cited

U.S. PATENT DOCUMENTS

| 8,338,410 B2 * | 12/2012 | Verleye et al. | ............ 514/229.8 |
| 2005/0233010 A1 | 10/2005 | Satow | |
| 2006/0004069 A1 * | 1/2006 | Momose et al. | ............ 514/383 |
| 2010/0063148 A1 * | 3/2010 | Christoph et al. | ............ 514/561 |

OTHER PUBLICATIONS

Ghirardi, "Chemotherapy-induced Allodinia: Neuroprotective Effect of Acetyl-L-carnitine", in vivo 19, 2005, pp. 631-638.*
French Search Report for FR 0951766.
Chiron Catherine: "Stiripentol.", Expert Opinion on Investigational Drugs, Jul. 2005, vol. 14, No. 7, pp. 905-911, XP002541844.
Shimizu Tadao et al: "Intrathecal lithium reduces neuropathic pain responses in a rat model of peripheral neuropathy", Pain, vol. 85, No. 1-2, Mar. 2000, pp. 59-64, XP002541845.
Stojkovic, T.; Donzé, C: "Neuropathies peripheriques. Le point sur les traitements symptomatiques", Neurologies, vol. 3, Sep. 2001, pp. 291-301, XP007909522.
Apfel Stuart C: "Neurotrophic factors and diabetic peripheral neuropathy", European Neurology, vol. 41, no. Suppl. 1, Feb. 1999, pp. 27-34, XP008110124.

* cited by examiner

*Primary Examiner* — Sreeni Padmanabhan
*Assistant Examiner* — Sahar Javanmard
(74) *Attorney, Agent, or Firm* — B. Aaron Schulman, Esq.; Stites & Harbison, PLLC.

(57) ABSTRACT

The present invention relates to a compound of the following formula (I):

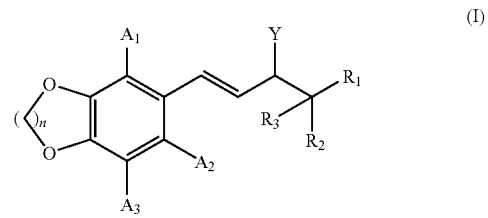

or a pharmaceutically acceptable salt thereof,
for use in the prevention or treatment of peripheral neuropathies.

20 Claims, 3 Drawing Sheets

COMPOUND FOR USE IN THE TREATMENT OF PERIPHERAL NEUROPATHIES

The present invention relates to a compound for use in the treatment of peripheral neuropathies.

Peripheral neuropathies, also referred to as peripheral neurites, concern peripheral nerve diseases as a whole. A distinction is made between asymmetrical peripheral neuropathies, which include single or multiple mononeuropathies, and symmetrical peripheral neuropathies or polyneuropathies.

As mentioned in the summary of professional recommendations relating to the diagnostic management of peripheral neuropathies, issued by the Haute Autorité de Santé (National Authority for Health) (HAS, France) in May 2007, peripheral neuropathies may become evident owing to:
- sensitive symptoms: paraesthesia, dysaesthesia, hypoaesthesia, pain, balance disorders, distal subjective symptoms;
- motor symptoms: weakness, in particular of the antero-external loculi of the legs, proximal or diffuse weakness, muscle cramps at rest or fasciculations, or
- neurovegetative symptoms: orthostatic or post-prandial discomfort, sweating disorders, micturition disorders, erection and ejaculation disorders, motor diarrhoea, sensation of gastric fullness, trophic symptoms, appearance of hyperkeratosis and then painless ulceration at the bearing points of the sole of the foot.

In children, the circumstances in which peripheral neuropathies become evident may be specific: writing disorders, areflexic hypotonia (in infants), motor acquisition retardation and valgus flat feet (in children less than 4 years old).

In general, the picture of a peripheral neuropathy is motor-sensory and symmetrical.

The most common aetiologies of peripheral neuropathies include, in particular, diabetes in the course of treatment, regular and excessive consumption of alcohol, and also chronic renal insufficiency. They may also be infectious neuropathies (in particular those caused by a zona), radiation-induced neuropathies, neuropathies associated with an inflammatory process, neuropathies following post-traumatic or post-surgical lesions (post-sciatic, for example), neuropathies associated with any previous family history of neuropathy, and neuropathies associated with the taking of certain medicaments, in particular of the following classes: antimitotics, antibiotics, antivirals, antiarrhythmics, antirheumatics, immunosuppressants, antipsychotics, antiepileptics, antileprosy drugs or antituberculous drugs.

More particularly as regards peripheral neuropathies caused by the taking of certain medicaments, these occur especially during anticancer chemotherapies. Indeed numerous medicaments used in those therapies, mainly those having cytostatic or antimitotic activity, cause a peripheral neuropathy which generally manifests itself as sensitive symptoms.

Thus, the main side effect of cisplatin, which is used in the treatment of various cancers, is to induce the appearance of sensitive peripheral neuropathies, in particular owing to the loss of sensitivity in the distal extremities, associated with axonal degeneration of the sensitive neurons (Thompson et al. (1984) Cancer 54:1269-1275).

The main response is to reduce the administered doses of those medicaments or else to interrupt treatment, which reduces their therapeutic efficacy accordingly.

It is therefore necessary to have available neuroprotective compounds capable of preventing or treating peripheral neuropathies, especially those associated with the taking of medicaments.

As such, Nerve Growth Factor (NGF) is the compound directed at the treatment of peripheral neuropathies on which the most information is available. Thus, it has been demonstrated in vitro that NGF combats the cisplatin-induced reduction of rat dorsal spinal ganglion neurite growth (Konings et al. (1994) Brain Res. 640:195-204), and in vivo, in mice, that NGF promotes the healing of a peripheral neuropathy induced by cisplatin (Aloe et al. (2000) Auton Neurosci. 86:84-93). However, the various clinical trials carried out on humans with NGF have not been conclusive, mainly because of the side effects associated with its use, which has led to envisage methods of administration by gene transfer (Chattopadhyay et al. (2004) Brain 127:929-939), the difficulties of implementation of which are well known.

It therefore remains to find an alternative compound to NGF for the treatment of peripheral neuropathies which is liable of being administered easily to humans.

Stiripentol (Diacomit), or 4,4-dimethyl-1-[(3,4-methylenedioxy)-phenyl]-1-penten-3-ol, is an antiepileptic indicated in severe myoclonic epilepsy in infancy, in addition to the combination of sodium valproate and clobazam when the latter proves to be insufficient in controlling crises (Chiron et al. (2000) Lancet 356:1638-1642).

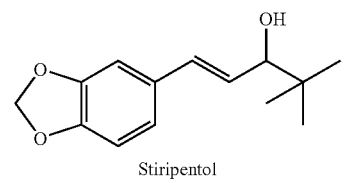

Stiripentol

Among its main effects, stiripentol inhibits the uptake of gamma-aminobutyric acid (GABA) and is also an inhibitor of several cytochrome P450 isoenzymes, especially CYP1A2 and CYP3A4 (Tran et al. (1997) Clin. Pharmacol. Ther. 62:490-504).

SUMMARY OF THE INVENTION

The present invention arises from the unexpected finding, by the inventors, that stiripentol has a neuroprotective effect equivalent to that of NGF in an in vitro model of peripheral neuropathy.

Thus, the present invention relates to a compound of the following formula (I)

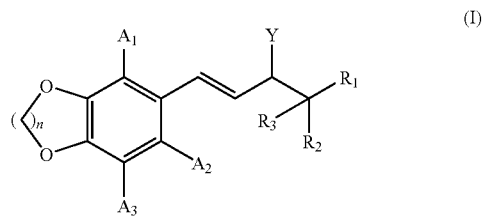

wherein:
n represents 1 or 2,
$A_1$, $A_2$ and $A_3$, which may be identical or different, represent a hydrogen atom, a halogen atom or a linear or branched alkyl group having from 1 to 4 carbon atoms,
$R_1$, $R_2$ and $R_3$ represent independently a hydrogen atom or a linear or branched alkyl group having from 1 to 4 carbon atoms, and Y represents —OH, =O or —SH;
or a pharmaceutically acceptable salt thereof,
for use in the treatment of peripheral neuropathies.

The present invention relates also to a method for preventing or treating peripheral neurophathies in an individual, wherein the individual is administered a prophylactically or therapeutically effective amount of a compound of formula (I) as defined above, or of a pharmaceutically acceptable salt thereof.

In one particular embodiment of the compound or of the method defined above, the compound of formula (I), or the pharmaceutically acceptable salt thereof, is combined with at least one additional compound intended for the prevention or treatment of peripheral neuropathies and/or with at least one additional cytostatic or antimitotic compound.

The present invention relates also to a pharmaceutical composition comprising as active substances at least one compound of formula (I) as defined above, or a pharmaceutically acceptable salt thereof, and at least one additional compound intended for the prevention or treatment of peripheral neuropathies and/or at least one additional cytostatic or antimitotic compound, optionally in combination with a pharmaceutically acceptable vehicle.

The present invention relates also to products containing:
  at least one compound of formula (I) as defined above, or a pharmaceutically acceptable salt thereof, and
  at least one additional compound intended for the prevention or treatment of peripheral neuropathies, and/or
  at least one additional cytostatic or antimitotic compound,
as a combination product for simultaneous, separate or staggered use in the prevention or treatment of peripheral neuropathies.

DETAILED DESCRIPTION OF THE INVENTION

Compounds of Formula (I)

Preferably, the above formula (I) is represented by the following formula (II):

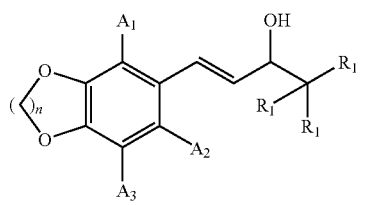

wherein n, $A_1$, $A_2$, $A_3$ and $R_1$ are as defined above.

More preferably, formula (I) or (II) above is represented by the following formula (III):

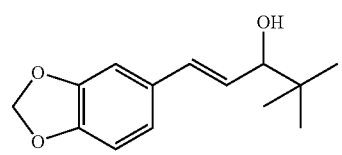

The compound of formula (III) is stiripentol or 4-dimethyl-1-[(3,4-methylenedioxy)-phenyl]-1-penten-3-ol.

As will be clearly apparent to the person skilled in the art, the formulae (I), (II), and (III) defined above represent the various stereoisomers covered by those formulae, or mixtures thereof, in particular racemic mixtures thereof.

Thus, the compound of formula (III) may be a compound of formula (IIIa), a compound of formula (IIIb), or a mixture of the compound of formula (IIIa) and the compound of formula (IIIb), in particular the racemic mixture thereof.

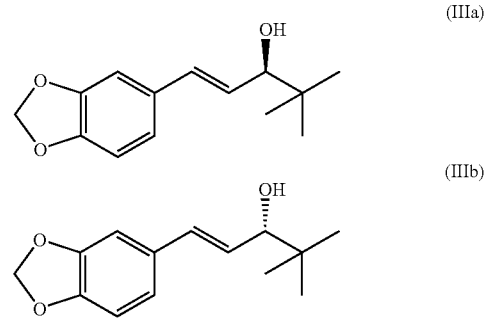

Of the preferred alkyl groups according to the invention, mention may be made in particular of the groups methyl, ethyl, n-propyl, isopropyl, n-butyl, s-butyl and t-butyl. Chlorine, iodine, bromine or fluorine atoms are preferred halogen atoms according to the invention.

The patent FR 2 173 691 describes the synthesis of stiripentol, in particular starting from (methylenedioxy-3,4-phenyl)-1-dimethyl-4,4-penten-1-one-3. The person skilled in the art could also readily synthesise the other compounds of formula (I) on the basis of that teaching.

Therapeutic Use

"Peripheral neuropathies" are well known to the person skilled in the art and are defined, in particular, in the summary of professional recommendations relating to the diagnostic management of peripheral neuropathies, issued by the Haute Autorité de Santé (National Authority for Health) (HAS, France) in May 2007 and in the article (Bouhassira (2008) Presse Med. 37:311-314) and also in the article (Bouhassira et al. (2008) Pain 136:380-7).

More especially, the neuropathies according to the invention may be asymmetrical or symmetrical peripheral neuropathies. Preferably, the peripheral neuropathies according to the invention are symmetrical.

Furthermore, the peripheral neuropathies according to the invention are preferably associated with, or manifest themselves as:
  sensitive symptoms: such as paraesthesia, dysaesthesia, hypoaesthesia, pain, balance disorders, or distal subjective symptoms; or
  motor symptoms: such as weakness, in particular of the antero-external loculi of the legs, proximal or diffuse weakness, muscle cramps at rest or fasciculations, or
  neurovegetative symptoms: such as orthostatic or postprandial discomfort, sweating disorders, micturition disorders, erection and/or ejaculation disorders, motor diarrhoea, a sensation of gastric fullness, trophic symptoms, the appearance of hyperkeratosis and then painless ulceration at the bearing points of the sole of the foot.

More preferably, the peripheral neuropathies according to the invention are associated with or manifest themselves as motor-sensory symptoms, in particular sensitive symptoms, and more especially pain.

The peripheral neuropathies according to the invention may, in particular, be associated with, result from, or be induced by diabetes in the course of treatment, regular and excessive consumption of alcohol, chronic renal insufficiency, an infection (infectious neuropathy), such as zona, irradiation (radiation-induced neuropathy), an inflammatory process, post-traumatic or post-surgical lesions, for example post-sciatic, any previous family history of neuropathy, and the taking of certain medicaments, in particular of the following classes: antimitotics, antibiotics, antivirals, antiarrhythmics, antirheumatics, immunosuppressants, antipsychotics, antiepileptics, antileprosy drugs and antituberculous drugs. However, it is preferred in the context of the present invention that the peripheral neuropathies be associated with, induced by or result from the taking of a medicament, in particular a cytostatic or antimitotic medicament.

Cytostatic or antimitotic medicaments or compounds are well known to the person skilled in the art. They are medicaments or compounds preventing or limiting cell multiplication or division. Those medicaments or compounds are especially indicated for the treatment of diseases in which abnormal cell multiplication occurs, such as cancers and proliferative diseases.

Preferably, the cytostatic or antimitotic medicaments or compounds according to the invention are selected from the group consisting of platinum derivatives, such as cisplatin, satraplatin, carboplatin, and oxaliplatin, and of vincristine, vinblastine, doxorubicin, and taxoids.

Posology and Administration

Preferably, the compound of formula (I) as defined above, or the pharmaceutically acceptable salt thereof, is administered at a unit dose of from 5 mg/kg to 100 mg/kg. In addition, the compound of formula (I) as defined above, or the pharmaceutically acceptable salt thereof, is preferably administered at a dose regimen of 10 mg/kg/d to 200 mg/kg/d.

Also preferably, the compound of formula (I) as defined above, or the pharmaceutically acceptable salt thereof, is administered in a form suitable for administration by the oral or rectal route. Thus, the compound of formula (I) as defined above, or the pharmaceutically acceptable salt thereof, is preferably presented in the form of a powder, sachets, tablets, gelatin capsules or suppositories.

Additional Compound

As understood here, compounds or products are "combined" or in "combination" when they are associated in such a manner that they can interact, or that their effects overlap in time, in the individual to whom they are administered. Thus, the compounds or products may be administered together, in the same pharmaceutical composition, or separately, that is to say, in different galenical forms and/or by different routes of administration and/or at different times or for different periods of administration.

When the compound of formula (I) as defined above, or the pharmaceutically acceptable salt thereof, is combined with at least one additional compound intended for the prevention or treatment of peripheral neuropathies, their administration is preferably such that their therapeutic effects accumulate, in an additive or synergistic manner.

Additional compounds intended for the prevention or treatment of the peripheral neuropathies according to the invention are well known to the person skilled in the art and are especially described in Stojkovic & Donzé (2001) *Neurologies* 3:291-301 and in the conference for consensus and recommendations of the *Canadian Pain Society* (2007) *Pain Res Manag.* 12:13-21. They are generally neuroprotective and/or analgesic compounds. Preferably, in the context of the present invention, the additional compound intended for the prevention or treatment of peripheral neuropathies is selected from the group consisting of NGF, BDNF, CNTF, IGF-I, NT-3 and L-carnitine.

BDNF (brain-derived neurotrophic factor), CNTF (ciliary neurotrophic factor), IGF-I (insulin-like growth factor-I) and NT-3 (neurotrophine-3) are described in particular in Apfel & Kessler (1995) *Bailliere's Clin. Neurol.* 4:593-606. L-carnitine is especially described in Uzun et al. (2005) *Electromyogr. Clin. Neurophysiol.* 45:343-51.

When the compound of formula (I) as defined above, or the pharmaceutically acceptable salt thereof, is combined with at least one additional cytostatic or antimitotic compound as defined above, their administration is preferably such that the effects of the compound of formula (I) as defined above, or of the pharmaceutically acceptable salt thereof, combat, by preventing them, limiting them, or by rectifying their consequences, the pro-neuropathic effects of the additional cytostatic or antimitotic compound.

DESCRIPTION OF THE FIGURES

FIG. 1 displays the effects of the vehicle (control), stiripentol (1, 3, 10 µM) and NGF (5 ng/ml) on the total length of the neurites (axis of ordinates, in µm) in the absence and in the presence of cisplatin (4.5 µg/ml) over a period of 24 hours.

Each column represents the mean±standard deviation from the mean (SDM, n=12 measurements per group).

The star symbol (*) represents p<0.05 compared with the respective controls (vehicle; without cisplatin); the sharp symbol (#) represents p<0.05 compared with the controls treated with cisplatin (ANOVA or Kruskall Wallis test followed by the Student Newman Keuls or Dunn test, respectively).

FIG. 2

Figure 2:
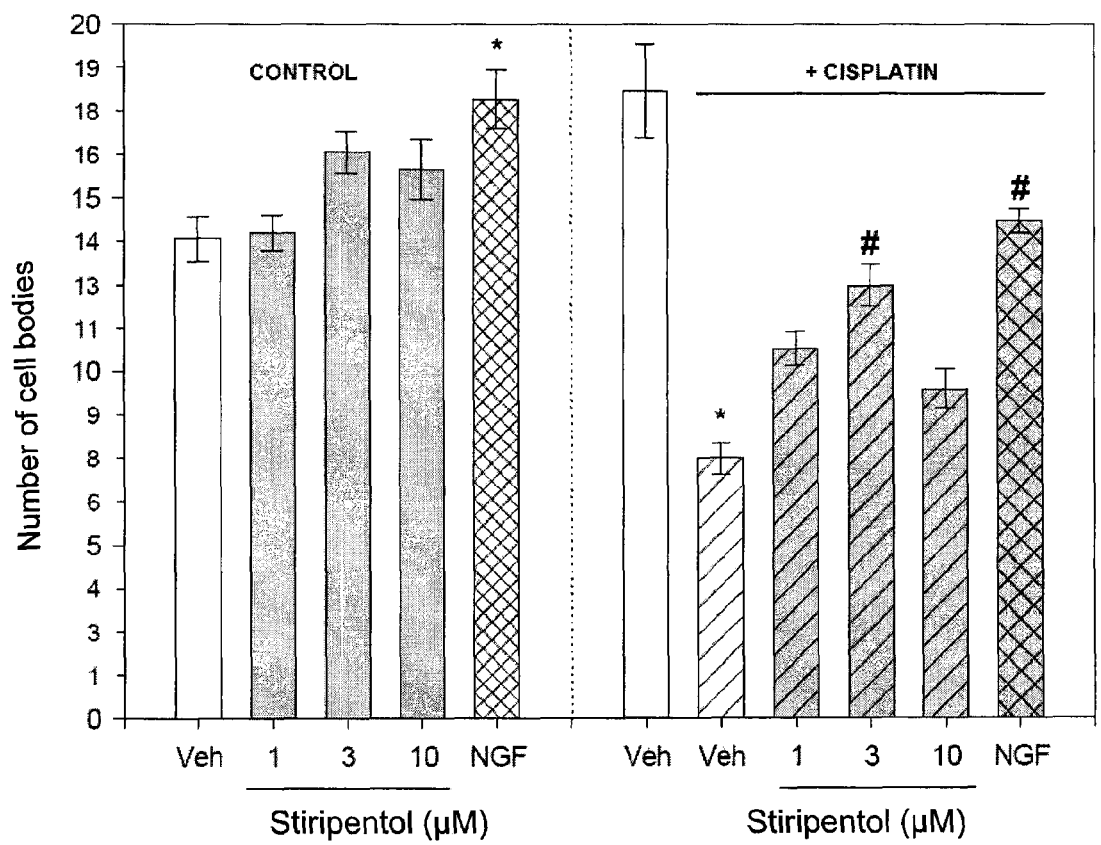

FIG. 2 displays the effects of the vehicle (control), stiripentol (1, 3, 10 µM) and NGF (5 ng/ml) on the number of cell bodies (axis of ordinates) in the absence and in the presence of cisplatin (4.5 µg/ml) over a period of 24 hours.

Each column shows the mean±SDM (n=12 measurements per group).

The star symbol (*) represents p<0.05 compared with the respective controls (vehicle; without cisplatin); the sharp symbol (#) represents p<0.05 compared with the controls treated with cisplatin (Kruskall Wallis test followed by the Dunn test).

FIG. 3

Figure 3:
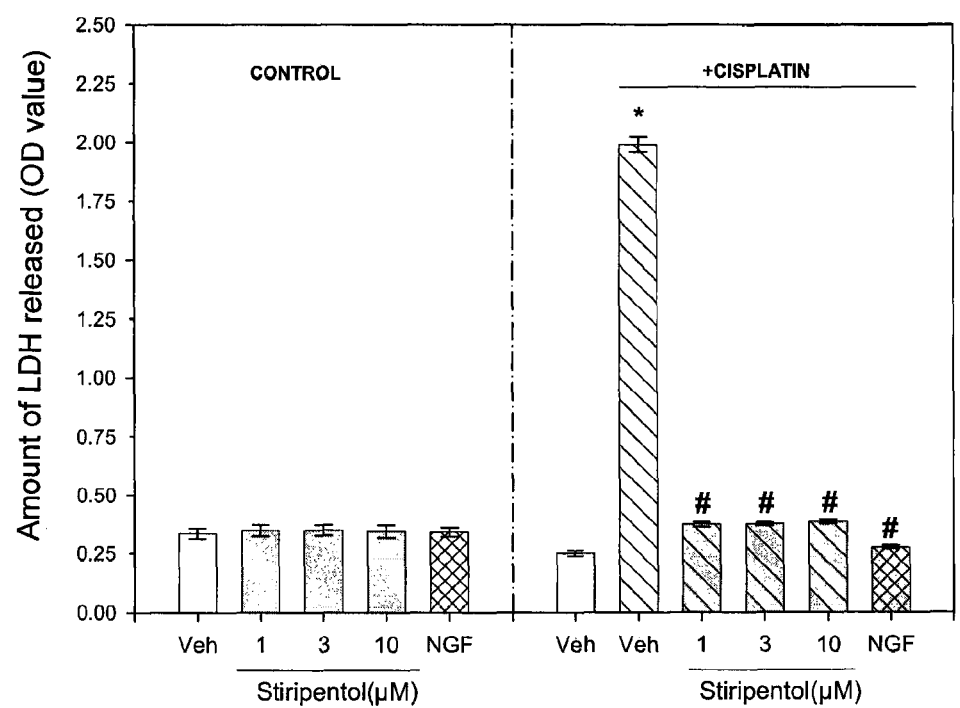

FIG. 3 displays the effects of the vehicle (control), stiripentol (1, 3, 10 µM) and NGF (5 ng/ml) on the cell release of LDH (axis of ordinates, optical density value (OD)) in the absence or in the presence of cisplatin (4.5 µg/ml) over a period of 24 hours.

Each column represents the mean±SDM (n=6 measurements/group).

The star symbol (*) represents p<0.05 compared with the respective controls (vehicle; without cisplatin); the sharp symbol (#) represents p<0.05 compared with the controls treated with cisplatin (Kruskall Wallis test followed by the Dunn test).

EXAMPLE

The principle of the study carried out by the inventors was to study the neuroprotective effects of stiripentol in an in vitro model of peripheral neuropathies. To be more precise, they studied the survival of sensitive neurons extracted from rat embryo dorsal spinal ganglions cultured in the presence of a cytotoxic agent, cisplatin, co-applied with stiripentol.

Methods

The co-culturing, for 5 days, of sensitive neurons (~5-10% of the cultivated cell population) associated with Schwann cells and fibroblasts (~95-90% of the cultivated cell population) is carried out in an appropriate medium as described in Hall et al. (1997) *J. Neurosci.* 17:2775-2784.

On the 5th day, the cell culture is incubated for 24 hours in the presence of DMSO (0.1%, liquid vehicle) and stiripentol (lot 162, Biocodex, France) at concentrations of 1, 3, and 10 µM or NGF (ref 13290-010 Invitrogen, France) (5 ng/ml), chosen as the reference product. Those various substances are associated or not with cisplatin (ref P4394, Sigma, France) (4.5 µg/ml).

The density of the neuritic networks (axons and dendrites) labelled by an anti-β-tubulin antibody (ref T8660, Sigma, France) is then determined by measuring their length, together with the number of cell bodies marked by means of an anti-MAP2 antibody (ref M4403, Sigma, France) as indicated by Gill & Windebank (1998) *J. Clin. Invest.* 101:2842-2850. Also determined is the amount of lactate dehydrogenase (LDH) (Kit de detection (detection kit), ref 1 644 793, Roche) released in the extracellular medium, the amount of which is proportional to the number of cells which are damaged or dead owing to the cisplatin-induced cell lysis, as indicated by Koh & Choi (1987) *J Neurosci Methods* 20:83-90.

Results

Figure 1:
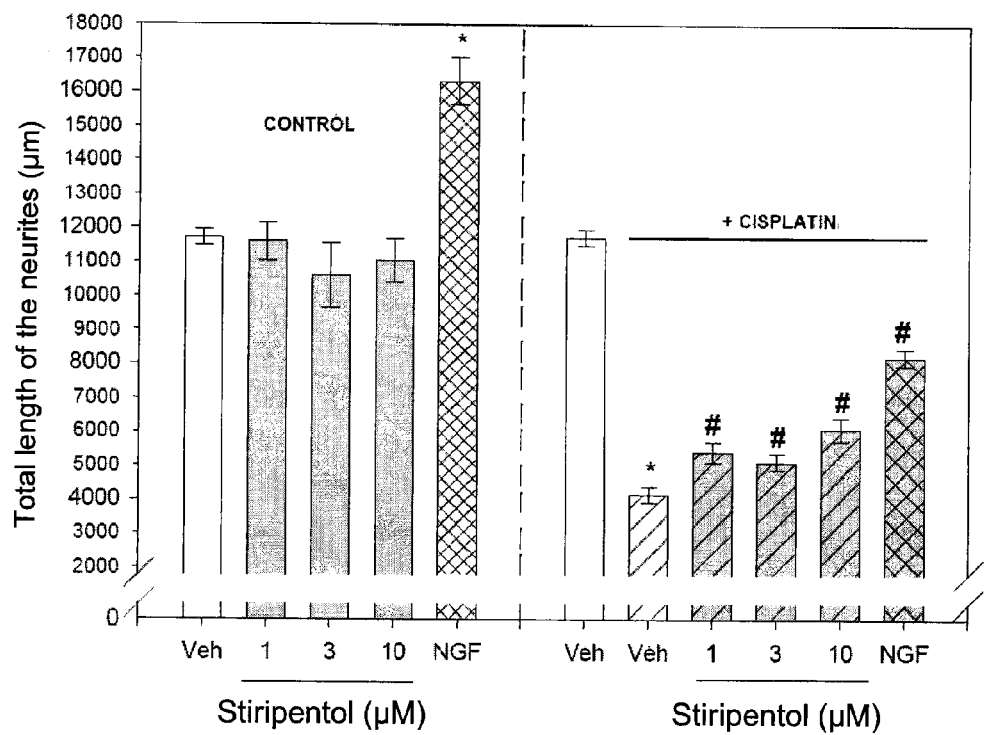
FIG. 1

As expected, cisplatin induces a reduction in the density of the neuritic networks (FIG. 1) and also a degeneration of the cell bodies (FIG. 2) which is associated with cell lysis (FIG. 3). In contrast, NGF at the concentration of 5 ng/ml has a neurotrophic activity (FIG. 1, FIG. 2) and a neuroprotective activity (FIGS. 1 to 3).

As regards stiripentol, its effect is to reduce the decrease in the density of the neuritic networks (FIG. 1) and in the number of neuronal cell bodies (FIG. 2) induced by cisplatin. In addition, the results obtained after the LDH assay reveal a neuroprotective effect of stiripentol (FIG. 3). Thus, in this in vitro model of peripheral neuropathy, stiripentol (1-10 µM) has a neuroprotective activity of the same order as that of NGF (5 ng/ml).

The invention claimed is:

1. A method for treating peripheral neuropathies in an individual, consisting of administering a therapeutically effective amount of a compound of the following formula (I):

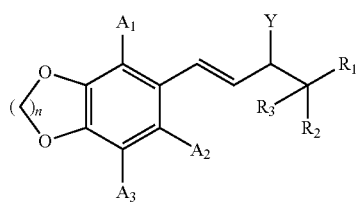

wherein:
n represents 1 or 2,
$A_1$, $A_2$ and $A_3$, which may be identical or different, represent a hydrogen atom, a halogen atom or a linear or branched alkyl group having from 1 to 4 carbon atoms,
$R_1$, $R_2$ and $R_3$ represent independently a hydrogen atom or a linear or branched alkyl group having from 1 to 4 carbon atoms, and
Y represents —OH, =O or —SH;
or a pharmaceutically acceptable salt thereof, to a patient in need thereof.

2. A method for treating peripheral neuropathies in an individual, comprising administering to an individual in need thereof a therapeutically effective amount of a compound of the following formula (I):

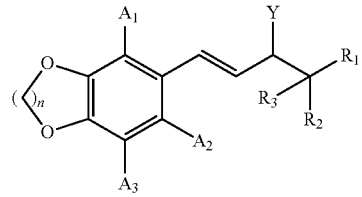

wherein:
n represents 1 or 2,
$A_1$, $A_2$ and $A_3$, which may be identical or different, represent a hydrogen atom, a halogen atom or a linear or branched alkyl group having from 1 to 4 carbon atoms,
$R_1$, $R_2$ and $R_3$ represent independently a hydrogen atom or a linear or branched alkyl group having from 1 to 4 carbon atoms, and
Y represents —OH, =O or —SH;
or a pharmaceutically acceptable salt thereof, wherein the compound or pharmaceutically acceptable salt thereof is not combined with at least one additional neuroprotective compound intended for the treatment of peripheral neuropathies.

3. The method according to claim 1, wherein the compound or pharmaceutically acceptable salt thereof is of the following formula (II):

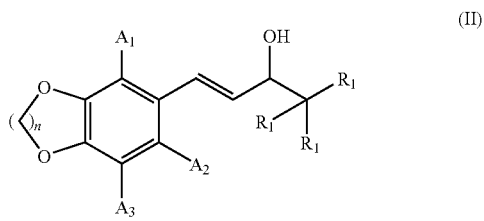

wherein n, $A_1$, $A_2$, $A_3$ and $R_1$ are as defined in claim 1.

4. The method according to claim 1, wherein the compound or pharmaceutically acceptable salt thereof is of the following formula (III):

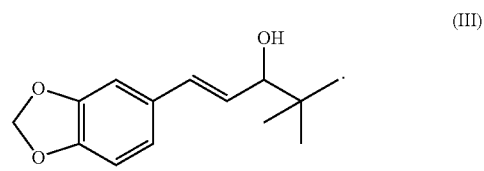 [SMILES: CC(C)(C)C(O)/C=C/c1ccc2c(c1)OCO2]

5. The method according to claim 1, wherein the peripheral neuropathy is associated with pain.

6. The method according to claim 1, wherein the peripheral neuropathy is associated with the taking of a medicament.

7. The method according to claim 6, wherein the medicament is cytostatic or antimitotic.

8. The method according to claim 1, wherein the compound or pharmaceutically acceptable salt thereof is administered at a unit dose of from 5 mg/kg to 100 mg/kg.

9. The method according to claim 1, wherein the compound or pharmaceutically acceptable salt thereof is administered at a dose regimen of from 10 mg/kg/d to 200 mg/kg/d.

10. The method according to claim 1, wherein the compound or pharmaceutically acceptable salt thereof is in a form suitable for administration by the oral or rectal route.

11. The method according to claim 1, wherein the compound or pharmaceutically acceptable salt thereof is in the form of a powder, sachets, tablets, gelatin capsules or suppositories.

12. The method according to claim 2, wherein the compound or pharmaceutically acceptable salt thereof is of the following formula (II):

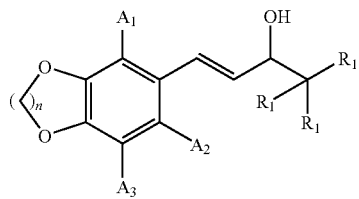

(II)

wherein n, $A_1$, $A_2$, $A_3$ and $R_1$ are as defined in claim 1.

13. The method according to claim 2, wherein the compound or pharmaceutically acceptable salt thereof is of the following formula (III):

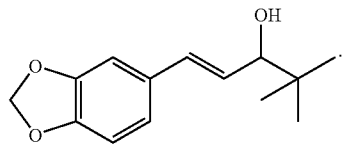

(III)

14. The method according to claim 2, wherein the peripheral neuropathy is associated with pain.

15. The method according to claim 2, wherein the peripheral neuropathy is associated with the taking of a medicament.

16. The method according to claim 15, wherein the medicament is cytostatic or antimitotic.

17. The method according to claim 2, wherein the compound or pharmaceutically acceptable salt thereof is administered at a unit dose of from 5 mg/kg to 100 mg/kg.

18. The method according to claim 2, wherein the compound or pharmaceutically acceptable salt thereof is administered at a dose regimen of from 10 mg/kg/d to 200 mg/kg/d.

19. The method according to claim 2, wherein the compound or pharmaceutically acceptable salt thereof is in a form suitable for administration by the oral or rectal route.

20. The method according to claim 2, wherein the compound or pharmaceutically acceptable salt thereof is in the form of a powder, sachets, tablets, gelatin capsules or suppositories.

* * * * *